United States Patent [19]

Hunt

[11] Patent Number: 4,473,071

[45] Date of Patent: Sep. 25, 1984

[54] COMBINATION HEAT EXCHANGER BREATHING AID AND MUFFLER

[76] Inventor: Patrick T. Hunt, R.R. 1, Box 146, Smithville, Mo. 64089

[21] Appl. No.: 404,339

[22] Filed: Jul. 30, 1982

[51] Int. Cl.[3] .......... A61M 15/00

[52] U.S. Cl. .......... 128/201.13; 128/204.17

[58] Field of Search .......... 128/201.13, 204.15, 128/204.17, 207.12

[56] References Cited

U.S. PATENT DOCUMENTS

| | | | |
|---|---|---|---|
| 1,359,631 | 11/1920 | Teed | 128/207.12 |
| 2,359,008 | 9/1944 | Smith | 128/207.12 |
| 4,269,183 | 5/1981 | Hunt | 128/201.13 |

*Primary Examiner*—Henry J. Recla
*Assistant Examiner*—Karin M. Reichle
*Attorney, Agent, or Firm*—Kokjer, Kircher, Bradley, Wharton, Bowman & Johnson

[57] ABSTRACT

A breathing device which provides for heat exchange relationship between exhaled air, body heat and inhaled air is the subject of the present invention. A mask is utilized to cover the mouth and nose of the wearer and this mask has an air intake port which is coupled with an air intake conduit. The conduit is provided with first, second, third and fourth conduit stretches which are adapted to be disposed around the neck of the wearer on opposite sides of the head. The air intake conduit is encased by a muffler which also extends around the head of the wearer. The muffler is provided with insulating means extending over a substantial portion of its surface and the insulating layer is provided with a highly reflective inner surface. Heat radiating from the body of the wearer will pass through the side of the muffler which is closest to the body where it undergoes heat exchange relationship with inhaled air passing through the conduits. This radiant heat will then be reflected by the aforementioned reflective surface for still further heat exchange. Meanwhile, exhaled air is also passed through the muffler to gain further heat exchange with the air passing through the intake conduits.

4 Claims, 4 Drawing Figures

A
B
3.
4.
10
12
14
16
18
20
22
24
25
26
27
28
28a
30
30a
32
34
36
38
40
42
44
46
48
50
52
60

COMBINATION HEAT EXCHANGER BREATHING AID AND MUFFLER

This invention relates generally to breathing assist devices and, more particularly, to a device which provides for heat exchange between exhaled and inhaled air and which is worn entirely around the neck.

Various breathing aid devices have been proposed in the prior art. Examples of typical breathing aids are found in U.S. Pat. Nos. 3,491,754; 3,707,966; and 4,062,359. All of the referenced patents disclose devices utilizing some type of conduit which is positioned next to the body for heat exchange relationship between the body and inhaled air.

Another prior art device is disclosed in U.S. Pat. No. 4,150,671. This device uses exhaled air for heat exchange relationship with inhaled air, but does not employ any means to take advantage of body heat.

An improved breathing aid is disclosed in my prior U.S. Pat. No. 4,269,183, issued May 26, 1981. While my prior device represents an improvement in breathing aids in that it takes advantage of air lost from the head as well as heat from exhaled air to warm incoming air, the device has one shortcoming in common with the other prior art constructions. It is relatively bulky and cumbersome to wear. It is also aesthetically unacceptable to some persons. Moreover, all of the prior art devices, including my own prior patented device, fail to provide any means to reflect radiant heat from the body back toward the air intake conduit after it has once passed outwardly away from this conduit.

It is, therefore, a primary object of the present invention to provide a breathing aid wherein exhaled air and body heat are utilized in a heat exchange relationship with inhaled air and the bulky and unattractive heat exchange bags heretofore associated with such devices are eliminated.

As a corollary to the above object, it is an aim of this invention to provide an air breathing aid of the type described which is worn entirely around the neck area and is therefore more aesthetically acceptable to the wearer.

Another very important object of my invention is to provide an air breathing aid which reflects heat radiating from the body back for further heat exchange relationship with the inhaled air.

Still another one of the aims of the invention is to provide a breathing device which utilizes body heat and exhaled air for heat exchange relationship with inhaled air and which has a greater capacity for inhaled air than devices previously available thereby offering less breathing resistance to the wearer during inhalation.

Still another object of the invention is to provide a breathing aid device having the features described in the foregoing aims and objects and which, as a result of the fact that it is worn entirely around the neck area, is easier to put on and take off than conventional devices worn in the chest or head area.

Other objects of the invention will be made clear or become apparent from the following description and claims when read in light of the accompanying drawing wherein:

Figures 1, 2, 3, 4:
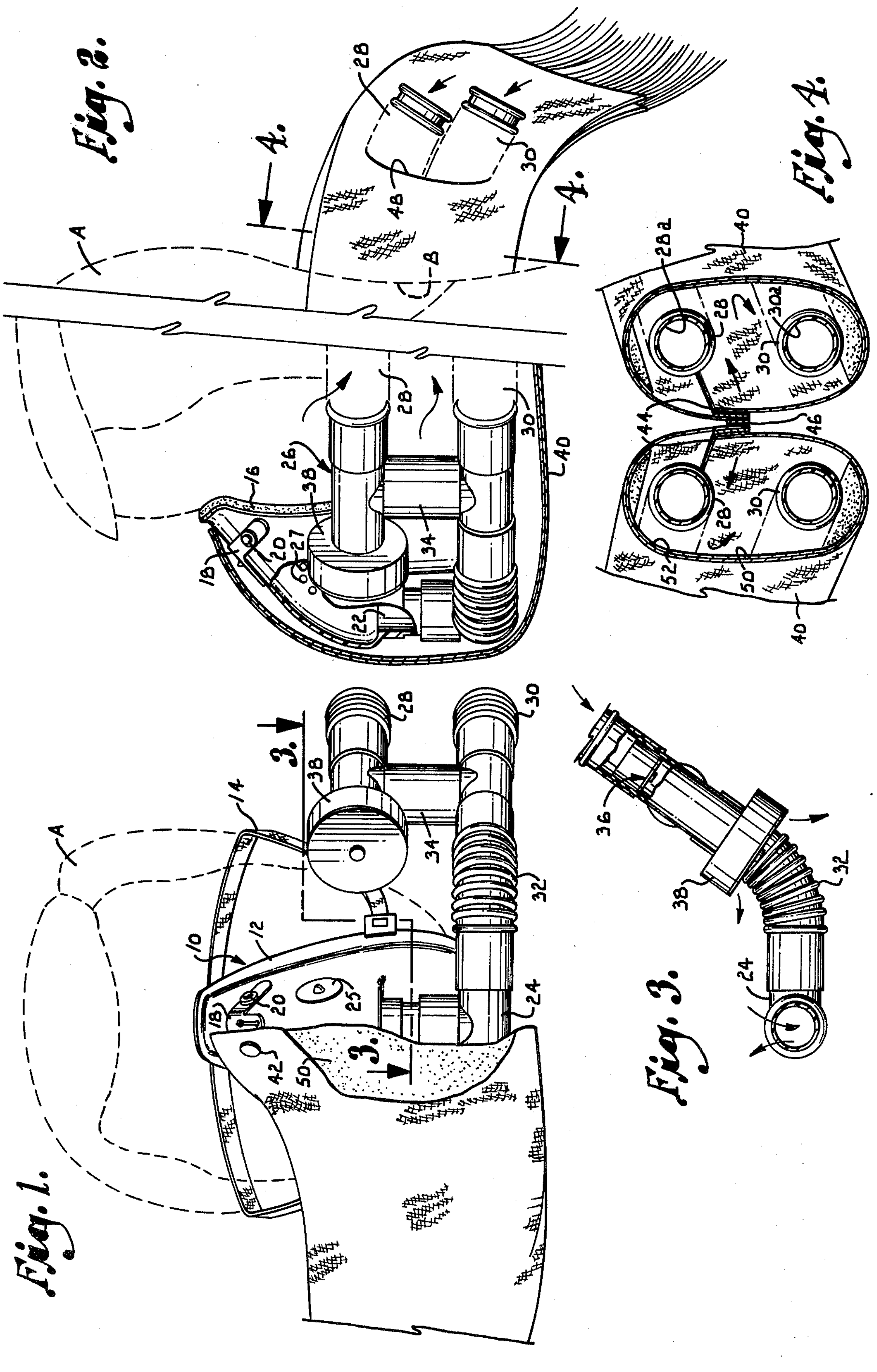
FIG. 1 is a front elevational view, with portions broken away, of the breathing aid of the present invention.
FIG. 2 is a side elevational view, with portions broken away, of the device shown in FIG. 1.
FIG. 3 is a horizontal cross-sectional view taken along line 3—3 of FIG. 1.
FIG. 4 is a vertical cross-sectional view taken along line 4–4 of FIG. 2.

Referring initially to FIGS. 1 and 2, the device of the present invention is designated generally by the numeral 10 and is designed to be worn around the head A of a person, more particularly in the area of the neck which is designated by the letter B is FIG. 2. Device 10 comprises a mask 12 designed to fit over the mouth and nose of head A and which is secured to the head by a strap 14. Mask 12 is provided with a peripheral strip 16 of resilient flexible material such as foam rubber. This flexible strip facilitates sealing of the mask to the face area.

Mask 12 is provided with a nose clip 18 which conforms the mask to the nose to assure proper fit. Clip 18 is provided with snaps 20 for purposes to be made clear hereinafter. The mask also has an intake port 22 which is coupled with a "T" connection 24 (FIG. 1). Mask 12 is provided with one way exhaust valves 25 disposed on opposite sides of the wearer's nose. Valves 25 allow air to exit from the mask via openings 27 but do not permit air to enter the mask.

Coupled with "T" connection 24 is an intake conduit designated generally by the numeral 26. Conduit 26 comprises first and third conduit stretches 28 and 30 disposed on one side of the head and coupled with "T" 24 by means of a short piece of flexible conduit 32. It is to be understood that conduit 26 also comprises second and fourth conduit stretches disposed on the opposite side of the head. As the second and fourth conduit stretches are identical to stretches 28 and 30, only the latter will be discussed and like reference numerals will be used on the second and fourth conduit sections.

Conduit sections 28 and 30 are joined together by and "I" coupled 34 which is also coupled with flexible conduit 32. It is to be noted from viewing FIG. 4 that the inner surfaces 28*a* and 30*a* of the respective conduit sections 28 and 30 are relatively smooth so as to facilitate the passage of air therethrough. While a plastic material will normally be used for conduits 28 and 30, a highly polished metal may also be employed to further enhance air flow as well as heat exchange characteristics. Each of conduit sections 28 and 30 is provided with a one-way flapper type of valve 36 positioned immediately downstream of "I" coupled 34. The details of construction of flapper valve 36 are shown and described in U.S. Pat. No. 4,269,183 which is incorporated herein by reference and, accordingly, these details will not be repeated herein. Another one-way flapper type valve 38 is coupled with one leg of "I" coupling 34 and is of larger diameter than conduit stretches 28 and 30. Valve 38 is of a size such that it is capable of exhausting a volume of air equal to the combined volume passing through conduit stretches 28 and 30 at any point in time. Valve 38 is of the same construction and operates in the same manner as valve 36.

Conduit 26 is encased within a muffler 40 which is of a length sufficient to extend around the entire neck area B. Snaps 42 of muffler 40 mate with snaps 20 to hold the muffler to mask 12. It is to be understood that muffler 40 is of a generally flat one-piece construction similar to that of a conventional muffler except that provision is made for joining the two sides of the muffler together. To this end, a releasable fastener strip 44 such as the interlocking cloth type material sold under the trademark Velcro is provided. Alternatively, the ends of the muffler may simply be tied together. A similar type of interlocking cloth fastener 46 is used at the back portion of the neck to hold the two lengths of muffler 40 around head A. Muffler 40 is also provided with two large openings 48 on opposite sides of the head through which the ends of conduit stretches 28 and 30 project. It may be desirable to provide an elastic band, tie string or other tensioning device around the perimeter of opening 48.

As best illustrated in FIG. 4, muffler 40 is provided with an insulating layer 50 which extends over approximately two-thirds of the inner surface of the muffler. Insulating layer 50 is characterized by an inner surface 52 of highly reflective material. A suitable material for constructing insulating layer 50 having a highly reflective inner surface is the material sold under the trademark Space Blanket. Insulating layer 50 is preferably secured to muffler 40 by stitching, adhesive tape or other suitable means.

When the device of the invention is to be used by a wearer, mask 12 is placed over the nose and mouth and secured by head strap 14. The two ends of muffler 40 are joined by fastener 46. As the wearer inhales, air will enter conduit stretches 28 and 30 travelling along the length of these stretches and entering mask 12 through intake port 22. As the wearer exhales, the force of air passing out through port 22, conduit 32 and "I" coupling 34 will cause valves 36 to close thus forcing the exhausted air out through valve 38. This exhausted air will be trapped inside of muffler 40 where it will undergo heat exchange with the incoming air passing through conduit sections 28 and 30. The exhausted air will eventually be discharged through the muffler since it is not air tight. Furthermore, body heat emanating from the neck and lower portion of the head of the wearer will pass through that portion of muffler 40 which is next to the body and which does not have insulating layer 40 next to it. The path of this radiant heat is indicated by arrows in FIG. 4. The radiant heat will undergo further heat exchange with incoming air passing through conduit stretches 28 and 30. The radiant heat will then be reflected by surface 52 back in the direction of the conduits where it undergoes still further heat exchange.

It has been found that the device of the present invention provides heat exchange capability which exceeds that of the prior art devices that utilize bulky and unattractive bags or headgear. Because the device of the present invention is worn entirely on the neck area, it is also possible to increase the volume of intake air by utilizing multiple intake conduits. This provides for greater ease and comfort in breathing. The device is also much easier to put on and take off since it is not required to remove the clothing or other wearing apparel.

I claim:

1. A breathing device adapted to be worn on the head and neck of a user and comprising:

a mask for covering the mouth and nose of a user, said mask having an intake port;

means for holding said mask in engagement with the face of a user;

air intake conduit means coupled with said intake port and comprising first, second, third and fourth conduits which are adapted to be disposed around the neck of a user, and each of said conduits having a first inlet end and an opposite second end;

said first and third conduits extending around the neck on one side of the head of a user and said second and fourth conduits extending around the neck on the opposite side of the head of a user;

coupling means for joining said intake port in fluid communication with said conduits at their said opposite second ends said coupling means including first and second I-shaped tubular couplings each having first and second ports coupled to said second ends of said conduits, a third port coupled to said intake port, a fourth port and a one-way exhaust valve coupled to said fourth port; and muffler means being adapted to be worn around the neck of a user and for substantially encasing said air intake conduit means;

said inlet ends of said air intake conduit means projecting through said muffler means at a point remote from said mask;

whereby air entering said inlet ends will pass through said conduit means in heat exchange with exhaled air passing through said exhaust valve and trapped by said muffler means.

2. A device as set forth in claim 1, wherein said muffler means includes a first portion adapted to be worn adjacent the neck area of said user and a second portion spaced from the first portion and connected thereto to define a space in which said intake conduits are encased, said air intake conduit means being positioned between said first and second portions, said muffler means further including an insulating layer lining the inside surface of said second portion and extending substantially over said second portion.

3. A device as set forth in claim 2, wherein said insulating layer includes a heat reflective surface extending substantially over said insulating layer on the side of the latter that is adjacent said air intake conduit means.

4. A device as set forth in claim 3, wherein is included means for holding said muffler around the neck of the wearer.

* * * * *